United States Patent [19]

Waldmann et al.

[11] 4,293,717

[45] Oct. 6, 1981

[54] PROCESS FOR PREPARING ALDEHYDES AND DIOLS

[75] Inventors: Helmut Waldmann; Wulf Schwerdtel, both of Leverkusen; Wolfgang Swodenk, Odenthal-Glöbusch, all of Fed. Rep. of Germany

[73] Assignee: Bayer Aktiengesellschaft, Leverkusen, Fed. Rep. of Germany

[21] Appl. No.: 9,019

[22] Filed: Feb. 5, 1979

Related U.S. Application Data

[63] Continuation of Ser. No. 743,546, Nov. 22, 1976, abandoned, which is a continuation of Ser. No. 563,263, Mar. 28, 1975, abandoned, which is a continuation of Ser. No. 322,321, Jan. 10, 1973, abandoned.

[30] Foreign Application Priority Data

Jan. 13, 1972 [DE] Fed. Rep. of Germany ....... 2201456

[51] Int. Cl.$^3$ ..................... C07C 47/21; C07C 47/20; C07C 29/03
[52] U.S. Cl. ................................. 568/485; 568/844; 568/850; 568/852; 568/860
[58] Field of Search ............... 568/485, 860, 852, 850, 568/844

[56] References Cited

U.S. PATENT DOCUMENTS

| | | | |
|---|---|---|---|
| 2,808,429 | 10/1957 | Cosby et al. | 568/485 |
| 3,231,620 | 1/1966 | Cotterill et al. | 568/485 |
| 3,972,944 | 8/1976 | Waldmann et al. | 568/485 |

*Primary Examiner*—Werren B. Lone
*Attorney, Agent, or Firm*—Sprung, Felfe, Horn, Lynch & Kramer

[57] ABSTRACT

Aldehydes and diols are prepared by reacting an olefine with hydrogen peroxide in the presence of a Group Va or VIa metal compound, such as molybdenum-(III)-acetylacetonate.

19 Claims, No Drawings

PROCESS FOR PREPARING ALDEHYDES AND DIOLS

This is a continuation of application Ser. No. 743,546, filed Nov. 22, 1976, which is a continuation of application Ser. No. 563,263, filed Mar. 28, 1975, which is a continuation of Ser. No. 322,321, filed Jan. 10, 1973, all now abandoned.

BACKGROUND

The invention relates to a process for the simultaneous production of aldehydes and diols from the respective olefines and hydrogen peroxide.

Aldehydes are important intermediate compounds in the synthesis of medicines or azo dyestuffs. Certain aldehydes, e.g. glutardialdehyde, are used as tanning agents.

Diols are important starting materials for the production of polyurethanes.

German Pat. No. 863,432 concerns the production of 1,2-diols from certain olefines and hydrogen peroxide in a direct reaction.

It is also known how to produce aldehydes by reacting 1,2-diols with oxidising agents, such as periodic acid (L. Malaprade, Bull.Soc. Chim. France (4) 43, 683 (1928)) or lead tetraacetate (R. Criegee, Ber.d.dtsch.-chem Ges. 64, 264 (1931)). However, it is only in exceptional cases that the direct reaction of olefines with such oxidising agents leads to satisfactory results. An additional factor is that these oxidising agents do not participate in the reaction as catalysts, but are consumed during the reaction. This means that the conversion products of the oxidising agents which have been introduced have to be isolated after the reaction has ended and converted into the corresponding starting compounds before they are used again.

SUMMARY

The invention concerns a process for the production of a diol and an aldehyde by reacting an olefine with hydrogen peroxide in the presence of a compound of a metal in Group Va or VIa of the Periodic Table.

DESCRIPTION

Olefines which can be considered for the process according to the invention are compounds of the general formula (I):

$R_1$ and $R_2$, which may be the same or different, can be hydrogen or a phenyl group optionally substituted by fluorine, chlorine, CN bromine, $C_1$–$C_6$-alkoxy or alkyl; or a straight-chain or branched alkyl radical optionally substituted by fluorine, chlorine, bromine, OH, $C_1$–$C_6$-alkoxy, carbo-$C_1$–$C_3$-alkoxy, CN or phenyl; or in which the radicals $R_1$ and $R_2$, together with the carbon atoms of the C—C double bond, can represent an optionally substituted carbocyclic ring with up to 24 carbon atoms.

The following are mentioned as examples of substituted phenyl groups: 4-chlorophenyl, 2,4-dichlorophenyl, 4-methoxyphenyl 4-chloro-2-methoxyphenyl, 4-propoxyphenyl, 4-tert.-butoxyphenyl 4-n-hexoxyphenyl, 4-bromo-3,5-di-tert.-butylphenyl,4-cyanophenyl, 4-cyano-3,5-dimethylphenyl.

The following are mentioned as examples of straight-chain or branched alkyl radicals: methyl, ethyl propyl, n-butyl, isobutyl, tert.-butyl,pentyl, hexyl,heptyl octyl, nonyl, decyl, undecyl, dodecyl, pentadecyl, hexadecyl, octadecyl and also their isomers.

The following are mentioned as examples of substituted alkyl radicals: chloromethyl, β-chloroethyl, (2 ethyl) hexyl, 2,4-diisopropyl-3-bromobutyl, hydroxymethyl, β-hydroxyethyl, ω-hydroxyhexyl, 2-hydroxymethylhexyl, β-methoxyethyl, 3-propoxypropyl, n-hexoxymethyl, 2,4,6-trimethoxyhexyl, 2-(methoxymethyl) propyl, carbomethoxymethyl, 3-(carbopropoxy) propyl, 3-(carbomethoxy) hexyl, 3-(β-carbomethoxyethyl)-butyl, β-cyanoethyl, 2-(β-cyanoethyl)propyl, ω-cyanoheptyl, ω-cyanooctyl.

The following are mentioned as examples of phenyl groups which are substituted by an alkyl radical; tolyl, ethyl, phenyl, propylphenyl, n-butylphenyl, tert.-butylphenyl, di-tert.-butylphenyl, tri-tert.-butylphenyl.

The following are mentioned as examples of alkyl radicals which are substituted by a phenyl radical; phenylmethyl, phenylethyl, phenylpropyl, phenyl-tert.-butyl, w-phenylhexyl.

The following olefins are mentioned as examples: ethylene, propylene 1-butylene 2-butylene, isobutylene, 1-pentene, 2-pentene, 1-hexene, 2-hexene, 3-hexene, 1-heptene, 2-heptene, 3-heptene, 1-octene, nonene, 1-decene, 2-decene, 1-undecene, 4-undecene, 5-decene, 2,5-dimethylhex-3-ene, 2,2,5,5-tetramethylhex-3-ene, 8-hexadecene, 1,4-di-fluorobutyl-2-ene, 1,2-di-trifluoromethyl-ethylene, 3-chloropropyl-1-ene, 4-chlorobutyl-1-ene, 3-chlorobutyl-2-ene, 1,4-dichlorobut-2-ene, 1,1,4,4-tetrachlorobut-2-ene, 6-chlorohex-1-ene, 1,6-dichlorohex-3-ene, 7-chlorohept-1-ene, 7,6-dichlorohept-2-ene, 1,7-dichlorhept-3-ene, 3,5,7-trichlorooct-1-ene, 1,8-dichlorooct-4-ene, 1,2-dicyclobutylethylene, 1,2-dicyclohexylethylene, 1,2-dicyclopentylethylene, 1,2-dicyclododecylethylene, 3-hydroxyprop-1-ene, 1,6-dihydroxyhex-3-ene, 3-methoxyprop-1-ene 1,4-dimethoxybut-1-ene, 1,6-dimethoxyhex-3-ene, 1,6-dipropoxyhex-3-ene, 1,10-dimethoxydec-5-ene, 1,10-dicarbohexoxydec-5-ene, 1,4-dicarbomethoxybut-2-ene, 1,8-dicarbomethoxyoct-4-ene, 1,8-dicarboethoxyoct-4-ene, 1,8-dicarbomethoxy-2,7-dicyclohexyloct-4-ene, 1,4-dicyanobut-2-ene, 1,6-dicyanohex-3-ene, 1-cyanopent-3-ene, 2-cyanopentene-3-ene. phenylethylene, 1,2-diphenylethylene, 1,4-diphenylbut-2-ene, 1,2-di-(p-chlorophenyl)ethylene, 1,2-di(p-methoxyphenyl)ethylene, 1,2-di-(2,4-dimethylphenyl)ethylene, 1,2-di-(p-cyclohexylphenyl) ethylene, 1,2-di(2-chloro-4-tert,-butylphenyl)ethylene, 1,2-di-(4-tert.-butylphenyl)ethylene, 1,4-divinylbenzene, 2,4-divinylbenzene, p-chlorophenylethylene, p-fluorphenylethylene.

Another preferred group of the general formula (I) corresponds to the formula (II):

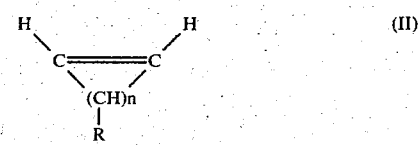

in which n is an integer from 3 to 10 and in which R, which may be the same or different for each of the carbon atoms to which it is bonded can be hydrogen, fluorine, chlorine, cyanide. $C_1$–$C_6$-alkoxy, $C_1$–$C_6$-alkyl, $C_5$–$C_7$-cycloalkyl or a phenyl group which is optionally substituted by fluorine, chlorine, cyanide or $C_1$–$C_6$-alkoxy.

The following are more particularly mentioned: cyclopentene, 3-chlorocyclopent-1,2-ene, 3,5-dichlorocyclopent-1,2-ene 4-hydroxycyclopent-1,2-ene, 3,5-dimethylclopent-1,2-ene 3,5-diethylcyclopent-1,2-ene, 4-isopropylcyclopen-1,2-ene, 4-tert.-butylcyclopent-1,2-ene, 3,5-diphenylcyclopent-1,2-ene 3,5-di-(4-chlorophenyl-cyclopent-1,2-ene, 4-phenylcyclopent-1,2-ene, 3-methoxycyclopent-1,2-ene, 4-propoxycyclopent-1,2-ene, 3,5-diisopropoxycyclopent-1,2-ene, 4-tert.-butoxycyclopent-1,2-ene, 4-n-hexoxycyclopent-1,2-ene, 3-carbomethoxycyclopent-1,2-ene, 4-carbopropoxycyclopent-1,2-ene, 3,5-di[(β-carbomethoxy)-ethyl]cyclopent-1,2-ene 3-cyanocyclopent-1,2-ene, 4-cyanocyclopentene, 4-(β-cyanoethyl)-cyclopent-1,2-ene, 3-fluorocyclopent-1,2-ene, 3-trifluoromethylcyclopent-1,2-ene, cyclohexene, 3-fluocyclohex-1,-ene, 3-trifluoxmethylcyclohex-1,2-ene, 3-chlorocyclohex-1,2-ene, 4-chlorocyclohex-1,2-ene 4,5-dichlorocyclohex-1,2-ene 3-hydroxycyclohex-1,2-ene, 3,5-dihydroxycyclohex-1,2-ene, 3-methylcyclohex-1,2-ene, 4-methylcyclohex-1,2-ene, 5-ethylcyclohex-1,2-ene, 4,5-di-n-hexylcyclohex-1,2-ene, 4-phenylcyclohex-1,2-ene, 4,5-diphenyl-cyclohex-1,2-ene 4-(p-chlorophenyl)-cyclohex-1,2-ene, 3-methoxycyclohex-1,2-ene 4-ethoxycyclohex-1,2-ene, 5-isopropoxycyclohex-1,2-ene, 4-hexoxycyclohex-1,2-ene, 4-(β-cyanoethyl)-cyclohex-1,2-ene, cycloheptene, 3-methylcycloheptene-1,2-ene, 3,7-dimethylcyclohept-1,2-ene, 4,5,6-trimethylcyclohept-1,2-ene, 5-tert.-butylcyclohept-1,2-ene 4,6-dichlorocyclohept-1,2-ene, 5-hydroxycyclohept-1,2-ene, 4,5-dihydroxycyclohept-1,2-ene, 3-phenylcyclohept-1,2-ene, 5-phenylcyclohept-1,2-ene, 4,6-di-[(p-tert.-butyl)phenyl]-cyclohept-1,2-ene, 3-methoxycyclohept-1,2-ene, 5-methoxycyclohept-1,2-ene, 3-propoxycyclohept-1,2-ene, 5-.tert-butoxycyclohept-1,2-ene, 3-carbomethoxycyclohept-1,2-ene, 4-carbomethoxycyclohept-1,2-ene, 3,7-dicarbomethoxycyclohept-1,2-ene, 5-(β-carbomethoxy)-ethylcyclohept-1,2-ene.

Cyclooctene, 3-chlorocyclooct-1,2-ene, 6,7-dichlorocyclooct-1,2-ene, 6-hydroxycyclooct-1,2-ene, 3-methyl cyclooct-1,2-ene 6,7-dimethycyclooct-1,2-ene, 4,8-dimethylcyclooct-1,2-ene, 6-phenylcyclooct-1,2-ene, 6-(p-chlorophenyl)-cyclooct-1,2-ene, 3-methoxycyclooct-1,2-ene, 3,8-dimethoxycyclooct-1,2-ene, 3-carbomethoxycyclooct-1,2-ene, 6,7-dicarbomethoxycycloot-1,2-ene cyclodecene, 3-chlorocyclodec-1,2-ene, 3,10-dichlorocyclodec-1,2-ene 6,7-dichlorocyclodec-1,2-ene, 3,4,8,9-tetrachlorocyclodec-1,2-ene 6-hydroxycyclodec-1,2-ene, 3-methylcyclodec-1,2-ene, 3,10-dimethylcyclodec-1,2-ene, 6,7-dimethyl-cyclodec-1,2-ene, 6-phenylcyclodec-1,2-ene, 3-carbomethoxycyclodec-1,2-ene, 3,10-dicarboethoxycyclodec-1 2-ene, 6-carbopropoxycyclodec-1,2-ene, 3-cyanocyclodec-1,2-ene, 6,7-dicyanoacyclodec-1,2-ene, cyclododecene, 10-chlorocyclodec-1,2-ene, 4,5-dichlorocyclodode-1,2-ene, 5,6,9,10-tetrachlorododec-1,2-ene, 3,5,6,9,10,12-hexachlorododec-1,2-ene, 3-methyldodec-1,2-ene 4-hydroxy-5-chlorocyclododec-1,2-ene, 3,6,11-trimethyldodec-1,2-ene 3-carbomethoxycyclododec-1,2-ene, 4-methoxycyclododec-1,2-ene, 4,9-methoxycyclododec-1,2-ene, 7-phenylcyclododec-1,2-ene It is preferably in the process according to the invention to use hydrogen peroxide in non-aqueous solution. Such solutions of hydrogen peroxide may be obtained in a known manner, for example, according to DAS No. 1,802,903. Another possible method for obtaining non-aqueous hydrogen peroxide solutions involves a solvent which is miscible with water and hydrogen peroxide and which, is added to the aqueous hydrogen peroxide solution, the water subsequently being removed, advantageously by distillation under vacuum. Esters, n-alkyl-substituted acid amides, alcohols, carboxylic acids, sulphonic acids and phosphoric acids are particularly to be considered here as solvents for hydrogen peroxide. The esters and alkylamides of phosphoric, phosphonic and phoshinic acids are found to be especially suitable. The following are mentioned as examples. Triethylphosphate, dimethylmethane phosphonate, dimethyl-β-cyanoethyl phosphonate, methyl-β-carbomethoxy phosphonate, trioctyl phosphate and trihexyl phosphate.

Another procedure for carrying out the process of the invention involves using a mixture of solvents, this being preferable to the use of a single solvent owing to the ability to simultaneously dissolve hydrogen peroxide, the added compound of a Group Va or VIa metal the olefine, and the aldehyde and diol which are fomed therefrom. Thus, it is advantageous to use initially, for example, a stock solution of hydrogen peroixide of relatively high concentration in a phosphonic acid ester or a phosphoric acid ester such as, for example, 30% hydrogen peroxide in dimethylmethane phosphonate, this solution having added to it an inert solvent, such as, for example, ethyl acetate, butyl acetate or methylene chloride, so that the solubility of the added compound of a Group Va or VIa metal and the olefine is increased.

A preferred operating procedure in the preparation of water-soluble aldehydes involves using hydrogen peroxide in a solvent which is immiscible, or has only limited miscibility, with ester, such as, for example, butyl acetate or trioctyl phosphate, and removing the reaction products after completing the reaction by extraction with water, so that aqueous solutions of the reaction products are obtained, which solutions are either further processed directly or from which the separate reaction products are isolated in a known manner.

The concentration of the non-aqueous solution of hydrogen peroxide which is introduced can fluctuate within wide limits and is in practice determined only by the limits imposed by explosion. Depending on the solvent, the upper limit of the hydrogen peroxide concentration will therefore lie between 30 and 60% by weight. Generally, non-aqueous solutions of hydrogen peroxides are used in the concentration range from 3 to 30% by weight, and concentrations from 10 to 20% by weight are preferred.

The reaction of the olefines is effected according to the invention by the addition of a compound of a Group Va or VIa metal. These are compounds of the metals vanadium, niobium, tantalum, chromium, molybdenum or tungsten compounds of molybdenum or vandium being preferred. Suitable compounds are the oxides, oxychlorides or the salts of these metals with organic acids, such as for example, acetates, benzoates, naphthenates or acetylacetonates. The following are mentioned as examples Vanadium-(II)-acetate, vanadium-(II)-acetylacetonate, vanadium-(II)-benzoate, vanadium-(II)-naphthenate, vanadium-(III)-acetate, vanadium-(III)-acetylacetonate, vanadium-(III)-benzoate, vanadium-(III)-naphthenate, vanadyl acetylacetonate, vanadyl naphthenate, niodium acetate, chromium-(II)-acetate, chromium-(II)-acetylacetonate, chromium-(III)-acetate, chromium-(III)-acetylacetone, chromium-(III)-naphthenate, molybdenum-(II)-acetylacetonate, molybdenum-(II)-acetate, molybdenum-(II)-benzoate, molybdenum-(III)-acetylacetonate, molybdenum-(III)-acetate, molybdenum-(III)-benzoate, molybdenum naphthenates, molybdenum acetylacetonates, tungsten-(III)-acetate and tungstyl acetyl acetonate.

Furthermore, complex compounds of the Group Va or VIa metals can be added, such as, for example, carbonyls, nitrosocarbonyls or carbonylates. Examples of these are molybdenum hexacarbonyl and chromium hexacarbonyl.

The quantity added of the Group Va or VIa metal compound can fluctuate within wide limits. Generally speaking, a sufficient quantity amounts to less than 10 mol-%, relative to the quantity of hydrogen peroxides introduced. It is usual to work with a quantity between 0.01 and 5 mol-%, relative to the introduced quantity of hydrogen peroxide, and a quantity between 1 and 2 mol-% is preferred. The compound of the Group Va or VIa metal can be either soluble or insoluble in the reaction mixture. It is also possible to add these metal compounds on inert supports, such as, for example, aluminium oxide, aluminium hydroxide, silica gel or zeolites.

The molar ratio of the olefine and hydrogen peroxide used in the solution can vary within wide limits. In order to obtained the complete reaction of the hydrogen peroxide, it is advantageous to use an olefine excess of from 1 to 1000 mol-% preferably from 10 to 100 mol-%.

The temperature at which the process according to the invention is carried out depends essentially on the stability of the hydrogen peroxide in the corresponding reaction mixture, the solvent and the added metal compound playing a part. Depending on the nature and the concentration of the added metal compound and the solvent, the reaction is carried out at a temperature of from $-80°$ and $+100°$ C., preferably in the range of from $-20°$ and $+60°$ C.

The pressure is established by the vapour pressure of the reactants and the solvent and is not critical for the course of the reaction.

The process according to the invention can be carried out both in the liquid and in the gaseous phase. The reaction time varies, depending on the olefine, the reaction temperature and the added compound on the Group Va or VIa metal. However, it is usually very short. Thus, the reaction has usually substantially ended after the reactants have been mixed and can be completed simply by additional stirring. The process according to the invention is generally carried out by initially mixing the olefine and the compound of the Group Va or VIa metal and then adding hydrogen peroxide while stirring, or initially mixing the hydrogen peroxide and the metal compound and then adding the olefine while stirring. A continuous operational procedure is also possible. The process according to the invention is carried out in known reactors which are suitable for such reactions, and allowance is made in a known manner for the catalytic effects of the wall of the reactor or of the foreign ions entering the solution because of corrosion.

The isolation of the 1,2-diols and of the aldehydes is well known and can be effected for example, by distillation. A preferred procedure for carrying out the process according to the invention is to perform the reaction in a solvent which is immiscible with water, such as, for example, trioctylphosphate, and to isolate the aldehydes and diols which are formed by extraction, optionally at boiling point with water from the reaction mixture.

The process according to the invention is illustrated in the following example.

EXAMPLE

Using a stainless steel stirrer-type autoclave, a mixture of 15.5 g of a 32.2% solution of $H_2O_2$ in dimethylmethane phosphonate, 5.1 g of cyclopentene and 0.8 g of molybdenum-(III)-acetylacetonate is heated for 3 hours at 60° C. The reaction mixture thus obtained has the following composition:

glutardialdehyde: 3.36 g
trans-cyclopentanediol: 1.10 g.

The values were obtained by gas chromatography, using a 2-meter column with 5% nitrile silicone on silanised, acid-washed kieselguhr with cyclohexyl acetate as an internal standard.

What we claim is:

1. Process for preparing a diol and an aldehyde which comprises reacting an olefin having the formula

wherein $R_1$ and $R_2$, which may be the same or different, are:
hydrogen;
phenyl which can be substituted by $C_1$–$C_6$ alkyl, $C_1$–$C_6$ alkoxy;
a straight-chain or branched alkyl, which can be substituted by $C_1$–$C_6$ alkoxy or phenyl;
or wherein the radicals $R_1$ and $R_2$ together with the C—C double bond represent a carbocyclic ring with up to 24 carbon atoms; with a non-aqueous solution of between 3 and 30% by weight hydrogen peroxide in an alcohol, ester, acid alkylamide or an ester of alkylamide or phosphoric, phosphonic or phosphinic acid solvent, in the presence of an acetate, benzoate, carbonyl, acetylacetonate or a naphthenate of a metal selected from the group of vanadium and molybdenum, at a temperature in the range of from $-80°$ to $+100°$ C., said metal compound being added in quantity of from 0.01 to 10 mol percent relative to the quantity of hydrogen peroxide.

2. Process of claim 1 wherein at least one of said $R_1$ or $R_2$ is substituted phenyl, substituted by $C_1$–$C_6$-alkoxy or an alkyl radical.

3. Process of claim 1 wherein at least one of said $R_1$ and $R_2$ is alkyl and said alkyl is substituted by $C_1$–$C_6$ alkoxy, carbo-$C_1$–$C_3$-alkoxy, or phenyl.

4. Process of claim 1 wherein at least one of said $R_1$ and $R_2$ is a straight-chain or branched alkyl and is selected from the group of methyl, ethyl, propyl, n-butyl, isobutyl, tert.-butyl, pentyl, hexyl, heptyl, octyl, nonyl, decyl, undecyl, dodecyl, pentadecyl, hexadecyl, octadecyl, isomers of the foregoing, 2-($\beta$-ethyl) hexyl, $\beta$-methoxyethyl, 3-propoxypropyl, n-hexoxymethyl, 2,4,6-trimethoxyhexyl, 2-(methoxymethyl) propyl, carbomethoxymethyl, 3-(carbopropoxy) propyl, 3-(carbomethoxy) hexyl, 3-(β-carbomethoxyethyl)-butyl, phenylmethyl, phenylethyl, phenylpropyl, phenyl-tert.-butyl and ω-phenylhexyl.

5. Process of claim 1 wherein $R_1$ and $R_2$ are selected from the group of 4-propoxyl phenyl, 4-tert.-butoxyphenyl, 4-n-hexoxyphenyl, ethylphenyl, propylphenyl, n-butylphenyl, tert.-butylphenyl, di-tert.-butylphenyl and tri-tert.-butylphenyl.

6. Process of claim 1 wherein the olefin is selected from the group of ethylene, propylene, 1-butylene, 2-butylene, isobutylene, 1-pentene, 2-pentene, 1-hexene, 2-hexene, 3-hexene, 1-heptene, 2-heptene, 3-heptene, 1-octene, nonene, 1-decene, 2-decene, 1-undecene, 4-undecene, 5-decene, 2,5-dimethylhex-3-ene, 2,2,5,5-tetramethylhex-3-ene, 8-hexadecene, 1,2-dicyclobutylethylene, 1,2-dicyclohexylethylene, 1,2-dicyclododecylethylene, 3-methoxyprop-1-ene, 1,4-dimethoxybut-1-ene, 1,6-dimethoxyhex-3-ene, 1,6-dipropoxyhex-3-ene, 1,10-dimethoxydec-5-ene, 1,10-dicarbohexoxydec-5-ene, 1,4-dicarbomethoxybut-2-ene, 1,8-dicarbomethoxyoct-4-ene, 1,8-dicarboethoxyoct-4-ene, 1,8-dicarbomethoxy-2, 7-dicyclohexyloct-4-ene, phenylethylene, 1,2-diphenylethylene, 1,4-diphenylbut-2-ene, 1,2-di(p-methoxyphenyl)ethylene, 1,2-di-(2,4-dimethylphenyl)-ethylene, 1,2-di-(p-cyclohexylphenyl)ethylene, 1,2-di-(4-tert.-butylphenyl)ethylene, 1,4-divinylbenzene, and 2,4-di-vinylbenzene.

7. Process of claim 1 wherein the olefin has the formula:

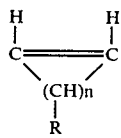

wherein n is an integer from 3 to 10, and R, which may be the same or different for each of the n carbon atoms to which it is bonded, can be hydrogen, $C_1$–$C_6$ alkoxy, $C_1$–$C_6$-alkyl, $C_{5-7}$-cycloalkyl or phenyl.

8. Process of claim 7 wherein phenyl is a $C_1$–$C_6$ alkoxy group.

9. Process of claim 7 wherein the olefin is selected from the group of cyclopent-1,2-ene, 4-hydroxycyclopent-1,2-ene, 3,5-dimethylcyclopent-1,2-ene, 3,5-diethylcyclopent-1,2-ene, 4-isopropylcyclopent-1,2-ene, 4-tert.-butylcyclopent-1,2-ene, 3,5-diphenylcyclopent-1,2-ene, 4-phenylcyclopent-1,2-ene, 3-methoxycyclopent-1,2-ene, 4-propoxycyclopent-1,2-ene, 3,5-diisopropoxycyclopent-1,2-ene, 4-tert.-butoxycyclopent-1,2-ene, 4-n-hexoxycyclopent-1,2-ene, 3-carbomethoxycyclopent-1,2-ene, 4-carbopropoxycyclopent-1,2-ene, 3,5-di[(β-carbomethoxy)-ethyl]-cyclopent-1,2-ene, cyclohexene, 3-methylcyclohex-1,2-ene, 4-methylcyclohex-1,2-ene, 5-ethylcyclohex-1,2-ene, 4,5-di-n-hexylcyclohex-1,2-ene, 4-phenylcyclohex-1,2-ene, 4,5-diphenylcyclohex-1,2-ene, 3-methoxycyclohex-1,2-ene, 5-isopropoxycyclohex-1,2-ene, 4-hexoxycyclohex-1,2-ene, cycloheptene, 3-methylcycloheptene-1,2-ene, 3, 7-dimethylcyclohept-1,2-ene, 4,5,6-trimethylcyclohept-1,2-ene, 5-tert.-butylcyclohept-1,2-ene, 3-phenylcyclohept-1,2-ene, 5-phenylcyclohept-1,2-ene, 4,6-di-[(p-tert.-butyl)-phenyl]-cyclohept-1,2-ene, 3-methoxycyclohept-1,2-ene, 5-methoxycyclohept-1,2-ene, 3-propoxycyclohept-1,2-ene, 5-tert.-butoxycyclohept-1,2-ene, 3-carbomethoxycyclohept-1,2-ene, 4-carbomethoxycyclohept-1,2-ene, 3,7-dicarbomethoxycyclohept-1,2-ene, 5-(β-carbomethoxy)-ethylcyclohept-1,2-ene, cyclooctene, 3-chlorocyclooct-1,2-ene, 3-methylcyclooct-1,2-ene, 6,7-dimethylcyclooct-1,2-ene, 4,8-dimethylcyclooct-1,2-ene, 6-phenylcyclooct-1,2-ene, 3-methoxycyclooct-1,2-ene, 3,8-dimethoxycyclooct-1,2-ene, 3-carbomethoxycyclooct-1,2-ene, 6,7-dicarbomethoxycyclooct-1,2-ene, cyclodecene, 3-methylcyclodec-1,2-ene, 3,10-dimethylcyclodec-1,2-ene, 6,7-dimethylcyclodec-1,2-ene, 6-phenylcyclodec-1,2-ene, 3-carbomethoxycyclodec-1,2-ene, 3,10-dicarboethoxycyclodec-1,2-ene, 6-carbopropoxycyclodec-1,2-ene, 3-methyldodec-1,2-ene, 3,6,11-trimethylyclododec-1,2-ene, 3-carbomethoxycyclododec-1,2-ene, 4-methoxycyclododec-1,2-ene, 4,9-methoxycyclododec-1,2-ene and 7-phenylcyclododec-1,2-ene.

10. Process of claim 7 wherein the olefin is cyclopentene or cyclohexene.

11. Process of claim 1 wherein hydrogen peroxide is in solution in an alcohol, acid, ester or acid alkylamide.

12. Process of claim 1 wherein the hydrogen peroxide is in solution in an ester or alkylamide of phosphoric, phosphonic or phosphinic acid.

13. Process of claim 1 carried out in the presence of molybdenum (III)-acetylacetonate.

14. Process according to claim 1 wherein an aldehyde is recovered from the resultant reaction mixture.

15. Process according to claim 1 wherein a diol is recovered from the reaction mixture.

16. Process according to claim 1 wherein $R_1$ and $R_2$, which may be the same or different, are hydrogen, phenyl which can be substituted by $C_1$–$C_6$ alkyl, $C_1$–$C_6$ alkoxy or straight chain or branched alkyl, which can be substituted by a $C_1$–$C_6$ alkoxy, or phenyl or wherein the radicals $R_1$ and $R_2$ together with the C—C double bond form a compound having the formula

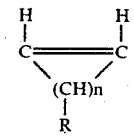

wherein
n is an integer from 3 to 10 and
R, which may be the same or different for each of the n carbon atoms to which it is bound, can be hydrogen, fluorine, chlorine, cyanide, $C_1$–$C_6$ alkoxy, $C_1$–$C_6$ alkyl, $C_5$–$C_7$ cycloalkyl or phenyl.

17. A process according to claim 1 wherein said process is carried out in the presence of a carbonyl of vanadium or molybdenum.

18. A process according to claim 17 wherein said carbonyl is molybdenum hexacarbonyl.

19. A process according to claim 1 wherein the olefin is cyclopentene.

* * * * *